United States Patent [19]

Day

[11] 4,135,505

[45] Jan. 23, 1979

[54] ORTHOPAEDIC FRACTURE FIXING APPARATUS

[75] Inventor: William H. Day, London, England

[73] Assignee: National Research Development Corporation, London, England

[21] Appl. No.: 787,475

[22] Filed: Apr. 14, 1977

[30] Foreign Application Priority Data

Apr. 30, 1976 [GB] United Kingdom ............. 17727/76

[51] Int. Cl.² .................... A61F 5/04; A61B 17/18
[52] U.S. Cl. ........................................... 128/92 A
[58] Field of Search .............. 128/92 A, 92 R, 84 R, 128/84 B, 85

[56] References Cited

U.S. PATENT DOCUMENTS

| 2,346,346 | 4/1944 | Anderson | 128/92 A |
| 3,961,854 | 6/1976 | Jaquet | 128/92 A X |

FOREIGN PATENT DOCUMENTS 851028 9/1939 France .................................. 128/92 A Primary Examiner—Ronald L. Frinks
Attorney, Agent, or Firm—Cushman, Darby & Cushman

[57] ABSTRACT

This invention concerns variably connectable orthopaedic fracture fixing apparatus of a kind comprising at least one elongate member, at least two universal joint assemblies for coupling said member and associated bone pins, and an adjustment assembly for adjusting the spacing between said joint assemblies when connected with said member. In the present case the joint assemblies are each of ball joint form in which a ball is clamped by a wedge action between two sockets. Also, the adjustment assemblies are not necessarily integrated with a fracture fixing network constructed with the apparatus, but are separable therefrom. In addition, the joint assemblies can receive bone pins in a variety of closely spaced positions to minimize any need to stress the pins.

6 Claims, 16 Drawing Figures

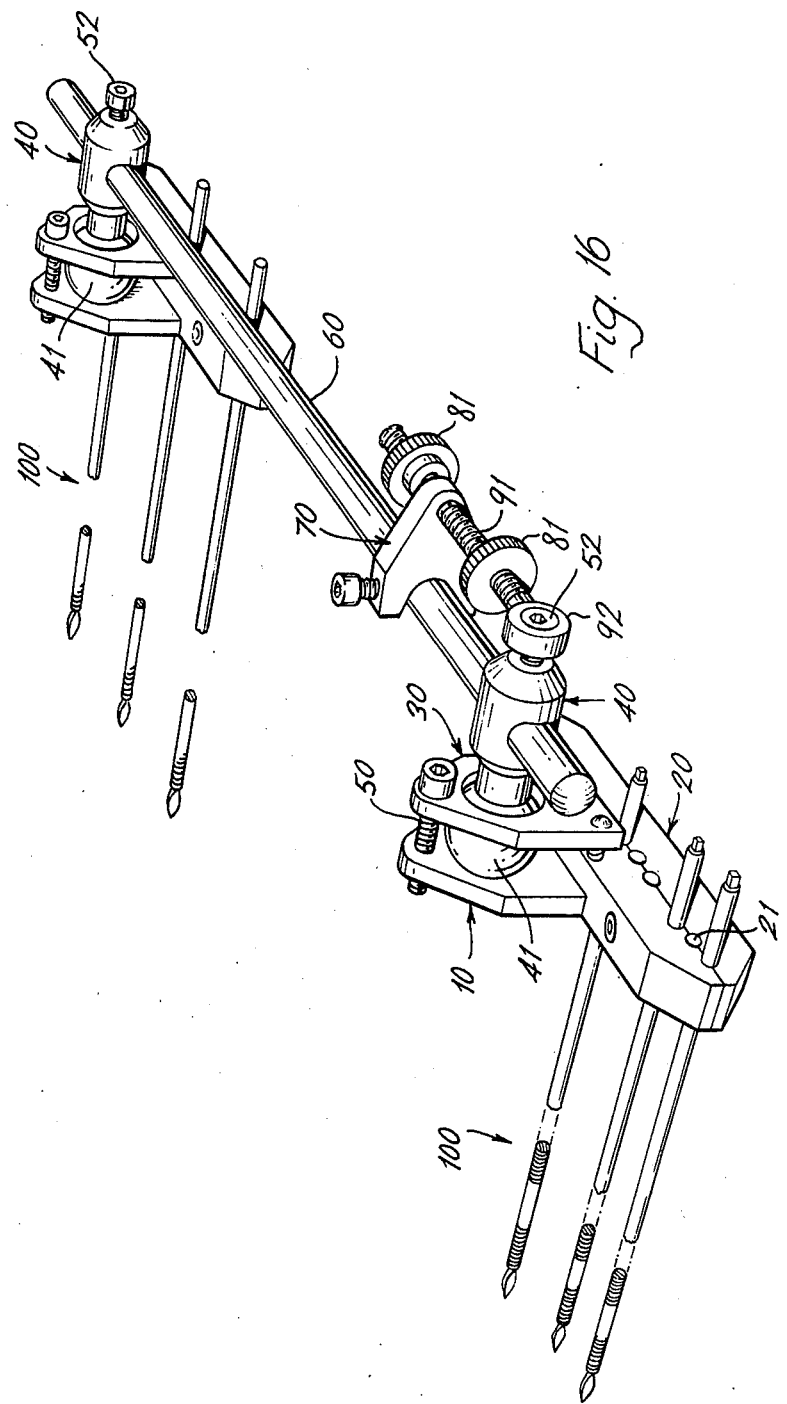

ORTHOPAEDIC FRACTURE FIXING APPARATUS

Various proposals have been made for orthopaedic fracture fixing apparatus comprising a range of components which are variably connectable with each other and with the fragments of a fractured bone by way of bone pins to form a support network holding the bone fragments in a desired positional relationship for the purposes of re-union. Such apparatus is also applicable to arthrodesis.

The kind of apparatus in question can be defined generally as comprising at least one elongate member, at least two universal joint assemblies for coupling said member and associated bone pins, and an adjustment assembly for adjusting the spacing between said joint assemblies when connected with said elongate member. Normally the apparatus will comprise a greater number of each of said assemblies and a range of elongate members for selective use in different combinations to suit different situations, and the above definition indicates a minimal apparatus.

Such apparatus offers advantage relative to the use of the traditional plaster cast support, but the few forms of the apparatus which have come into regular clinical use are not without their own disadvantages. These disadvantages result in a common need to employ unduly complex and/or duplicated networks in order to attain a desired rigidity of support. This, in turn, means that an extensive, and therefore costly, range of components must be made available. Also, a result is to reduce one of the initially sought-after advantages, namely, access to the fracture site.

An object of the present invention is to improve this situation, and this is achieved by providing apparatus of the above kind in which, inter alia, the universal joint assemblies are of ball joint form in which a ball is clamped by a wedge action.

For a fuller and clearer understanding of the invention, reference is made to the accompanying drawings which illustrate parts of a presently preferred embodiment of the invention, and in which:

FIGS. 1 and 2 respectively illustrate in plan and a side elevation a first component of a universal joint assembly;

FIGS. 3 and 4 respectively illustrate in a side elevation and underneath plan a second component of said assembly;

FIGS. 5 and 6 respectively illustrate in a side elevation and an end elevation of third component of said assembly;

Figure 1:
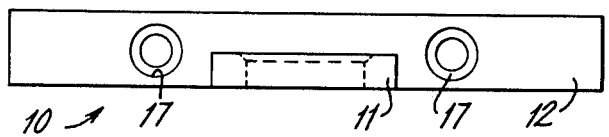
Figure 2:
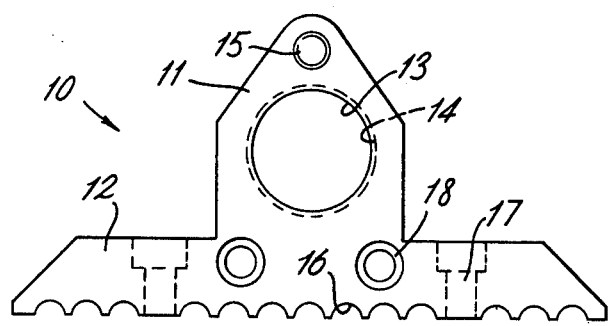
Figure 3:
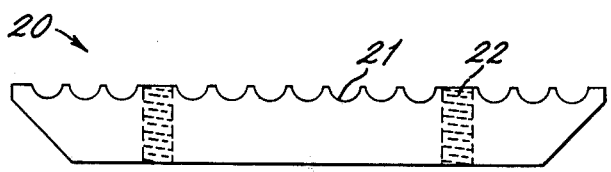
Figure 4:
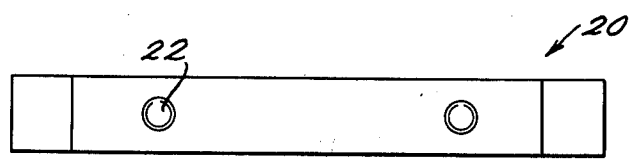
Figure 5:
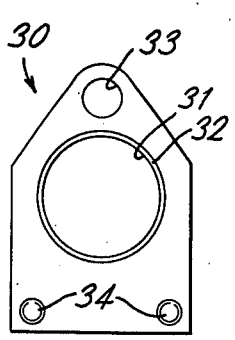
Figure 6:
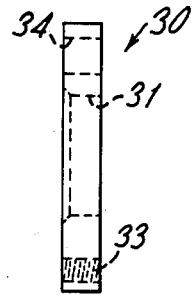
Figure 7:
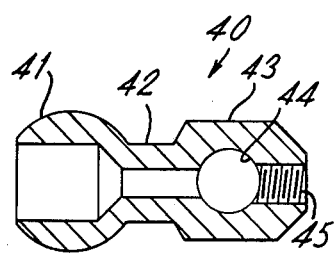
FIG. 7 illustrates in a cross-section a fourth component of said assembly.
Figure 8:
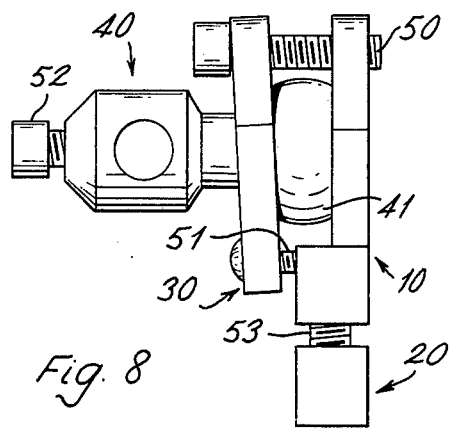
FIG. 8 illustrates in an end elevation a universal joint assembly made with the components of FIGS. 1 to 7.
Figure 9:
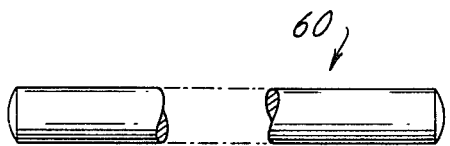
FIG. 9 illustrates in side elevation an elongate member for connection with said assembly of FIG. 8.
Figure 10:
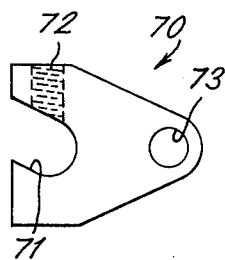
Figure 11:
Figure 12:
Figure 13:
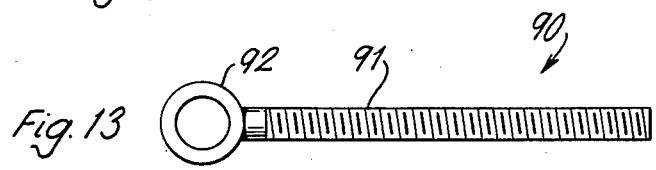
Figure 14:
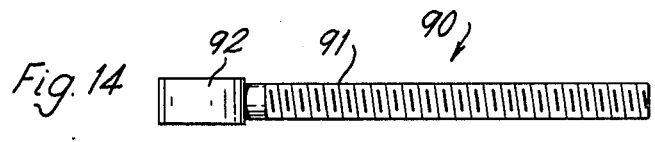
Figure 15:
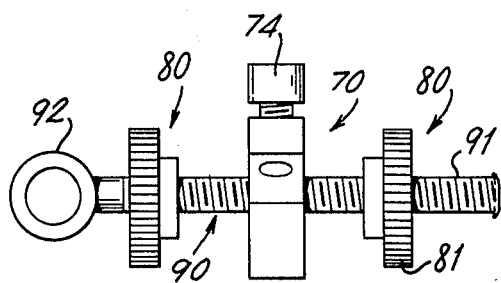

FIGS. 10 and 11 respectively illustrate in an end elevation and a side elevation a first component of an adjuster assembly;

FIG. 12 illustrates, in partly-sectioned side elevation, one of two like second components of said adjuster assembly;

FIGS. 13 and 14 respectively illustrate in a side elevation and plan a third component of said adjuster assembly;

FIG. 15 illustrates in side elevation an adjuster assembly made with the components of FIGS. 10 to 14; and FIG. 16 illustrates in a perspective view an apparatus comprising the assemblies of FIGS. 8 and 15, the member of FIG. 9, and a plurality of bone pins.

The first component of the universal joint assembly is a plate 10 of inverted T-shape, the T-stem portion 11 of this plate being of lesser thickness than the T-crossbar portion 12. The stem portion 11 is formed with a larger circular opening 13 which has a conical chamfer 14 around its periphery on one side of the plate. The stem portion 11 is also formed adjacent its free end with a smaller threaded circular bore 15. The crossbar portion 12 is formed in its longitudinal free edge with a parallel array of part-circular-cylindrical recesses 16 extending transversely thereacross. These recesses are all of like radius equal to that of a conventional bone pin and just less than semi-circular cross-sectional extent. The recesses are arranged in three groups in which successive recesses are mutually spaced by a distance less than their radius. The portion 12 is also formed with two circular bores 17 which respectively pass between the spaces intermediate the groups of recesses 16 to emerge in the opposite edge of the portion, where these bores are counterbored. Lastly, the portion 12 is formed with two further circular bores 18 passing transversely therethrough adjacent its junction with the stem portion 11, these bores 18 each being counterbored at its corresponding end opposite to the chamfer 14.

The second component of the universal joint assembly is a plate 20 similar to the crossbar portion 12 of the first component in so far as this plate has corresponding shape and thickness, and has an array of like recesses 21 along one edge which correspond to the recesses 16. The plate 20 also has two threaded bores 22 therethrough which align with the bores 17 when the plate is abutted with the first component to align the recesses 16 and 21.

The third component of the universal joint assembly is a plate 30 similar to, but longer than, the stem portion 11. This plate has an opening 31 with a chamfer 32 respectively corresponding to the opening 13 and chamfer 14, and three bores 33, 34, and 34 which can be respectively aligned with the bores 15, 18 and 18 when the openings 31 and 13 are aligned. The bores 34 are threaded.

The fourth component of the universal joint assembly is generally in the form of a body of revolution 40 comprising a coaxial connection of a ball portion 41, a necked portion 42, and a connector portion 43. The ball portion 41 is externally shaped as a major spherical segment, and the other portions generally as circular cylinders, the whole being axially hollowed by boring, the connector portion being diametrically bored at 44, and the free end 45 of the axial bore in the connector portion being threaded up to the bore 44. The ball and connector portions have diameters respectively greater than and less than that of the openings 13 and 31 in the first and third components.

The four components described so far are assembled as shown in FIG. 8. The connector portion 43 of the body 40 is passed through the opening 31 of the plate 20 to seat the ball portion 41 in the chamfer 32. The plate 10 is then located to seat the chamfer 14 of its opening 13 against the ball portion 41, opposite to the plate 20; the bores 15, 18 and 18 and 33, 34, 34 are aligned to receive respective bolts 50, 51 and 51; and these bolts are tightened on the ball portion to render the plates substantially parallel, whereat the bolts 51, 51 are made captive by rivetting over, with subsequent adjustment of the joint involving loosening of bolt 50. A further bolt 52 is located in the bore 45 of body 40, and two bolts 53 are employed to connect the plate 20 to plate 10 with their recesses 21 and 16 in facing disposition. The heads of the bolts 51 and 53 seat in their respective counterbores, and all of the bolts have like recessed heads for co-operation with a common driver tool.

The elongate member of FIG. 9 is a circular cylindrical rod 60 with diameter such as to afford a close sliding fit in the bore 44, the rod being securable in this bore by tightening bolt 52.

The first component of the adjuster assembly is a plate 70 having an inclined semi-circularly ended slot 71 formed in an edge thereof, this slot having a width corresponding to the diameter of the rod 60. A threaded bore 72 is formed in another edge of the plate 70, this bore opening into the slot 71. The plate 70 is also formed with another bore 73 which passes transversely therethrough.

The second components of the adjuster assembly are each in the form of nuts 80 having knurled flanges 81.

The third component of the adjuster assembly is in the form of a bolt 90 having a threaded shaft 91 which terminates at one end in a head in the form of a ring 92. The ring 92 is dimensioned to receive the head of the bolt 52 of the universal joint assembly, the thread of shaft 91 complements those of nuts 80, and the shaft diameter corresponds to that of bore 73.

The last four components are assembled as shown in FIG. 15 with the bolt shaft 91 passed through the bore 73 of plate 70, the nuts 80 threadably located on the shaft 91 on opposite sides of the plate 70, and this assembly rendered captive by rivetting over the end of the bolt shaft. A bolt 74 similar to those already mentioned is located in the threaded bore 72 of the plate 70.

The apparatus of FIG. 16 comprises a rod 60 having a respective universal joint assembly of FIG. 8 connected to each end portion thereof. Each such joint assembly has a plurality of bone pins 100 connected between its plates 10 and 20, these pins being seated between corresponding pairs of the recesses 16 and 21. The rod 60 and one of the joint assemblies are coupled by an adjuster assembly, the adjuster assembly being connected to the rod by receipt of the latter in the slot 71 of the plate 70, and to the joint assembly by receipt of the head of bolt 52 in the ring 92.

In use of such an apparatus two fragments of a fractured bone each have a group of bone pins 100 secured thereto, suitably by use of an appropriate drill and jig, to form a substantially planar parallel array. Each group of pins is located in a joint assembly as shown and the bolts 53 tightened to secure the same together. The bone fragments are adjusted, if necessary, to an appropriate positional relationship; the joint assemblies are adjusted to receive the rod 60 as shown, and then locked by tightening the bolts 50; one of the joint assemblies is secured with the rod 60 by tightening the respective bolt 52; the adjuster assembly is coupled between the rod and other joint assembly as shown, and secured to the rod by tightening bolt 74; the adjuster assembly is secured by tightening the nuts 80 on to the plate 70, and in so doing, any final adjustment of bone fragments positions can be made, such as to produce compression or distraction therebetween; and thereafter the second joint assembly can be secured to the rod 60 by tightening the respective bolt 52, and the adjuster assembly disconnected.

It is to be noted that the apparatus just described is, as mentioned earlier, a minimal arrangement and it may be amplified by the provision of additional members and assemblies. Also the apparatus may be augmented by different parts, such as universal joint assemblies serving to interconnect elongate members one to another.

Turning now to consideration of the more general advantages of the presently proposed apparatus as exemplified by the illustrated embodiment: these arise from several features. Firstly, it is to be noted that the apparatus comprises a universal joint assembly of ball joint form in which a ball is clamped by a wedge action between two sockets. This contrasts with the form of joint commonly used in prior apparatus, which form is compounded from sub-assemblies affording only a single degree of freedom for the purposes of adjustment, and which sub-assemblies are typically clamped by abutting two planar surfaces subject to force perpendicular thereto. The proposed ball joint is inherently more rigid and involves fewer components than the prior joints.

Secondly, it is to be noted that the adjuster assembly of the proposed apparatus need not form part of a finalized network, but is separable therefrom and can be used successively in different locations of a network during construction thereof. This contrasts with the prior apparatus which commonly employ adjuster mechanisms integrated with the associated elongate members and require the latter members to be at least partly threaded for the purposes of screw connections. Again, then, the proposed apparatus allows a reduction and simplification of components to be effected and, in addition, rigidity is enhanced by the exclusion of compound screw-connected elongate members.

A third advantageous feature arises from the relatively close spacing of the recesses in which the bone pins are secured. While the bone pins are normally located in the bone fragments by a procedure involving a jig, it is difficult to maintain a precisely predetermined positional relationship between the free end portion of the pins which are to be connected with the network. The spacing of the relevant recesses in the present apparatus is chosen to facilitate engagement in the recesses with a minimum requirement for bending or stressing of the pins. This contrasts with the prior apparatus in which the bone pin recesses are relatively widely spaced.

I claim:

1. Orthopaedic fracture fixing apparatus for use in association with two sets of bone pins respectively located on opposite sides of a fracture, said apparatus comprising:

an elongate member;

two universal joint assemblies respectively connected with opposite end portions of said elongate member;

each of said universal joint assemblies including a pair of plates and a ball with a radial projection therefrom, said projection having lateral dimensions less than the diameter of said ball, said projection being apertured and receiving said elongate member in sliding engagement, said projection receiving a screw to clamp said elongate member therein, each of said plates having an aperture with lateral dimensions less than said ball diameter, one of said plate apertures having lateral dimensions greater than those of said projection to allow passage of the latter through the former, said plates receiving screws to clamp said ball therebetween with said ball seated in said plate apertures and with said projection passing through said one plate aperture, and one of said plates being further apertured in a plurality of locations to receive one of said bone pin sets, and said one plate receiving further screws to clamp said one bone pin set therein;

and an adjustment assembly connected between one of said universal joint assemblies and said elongate member to adjust the mutual spacing of said universal joint assemblies along said elongate member.

2. Apparatus according to claim 1 wherein said ball is spherically-shaped and said plate apertures are of circular cylindrical shape with an outwardly divergent conical chamfer at one end thereof.

3. Apparatus according to claim 1 wherein said one plate is in two parts which each have a straight edge portion with a similar sequence of part-cylindrical recesses formed transversely thereacross, said plate parts being screw connected to clamp said one set of bone pins in individual manner between corresponding pairs of said recesses, and each of said sequences includes at least one group of like recesses successively spaced by a distance which is less than the extent of each said like recess along the relevant plate part edge.

4. Apparatus according to claim 3 wherein all of said recesses are of like part-circular-cylindrical form with cross-sectional extent less than a semi-circle, and said distance is less than the radius of said cylindrical form.

5. Orthopaedic fracture fixing apparatus for use in association with two sets of bone pins respectively located on opposite sides of a fracture, said apparatus comprising:

an elongate member;

two universal joint assemblies respectively connected with opposite end portions of said elongate member and to couple said elongate member with respective ones of said bone pin sets;

and an adjustment assembly connected between one of said universal joint assemblies and said elongate member to adjust the mutual spacing of said universal joint assemblies along said elongate member;

said adjustment assembly including:

a bolt with a head of apertured form in freely encompassed coupling with one of said universal joint assemblies;

a plate apertured and receiving said bolt in sliding engagement and having a slot along its edge and said plate receiving said elongate member in such slot and receiving a screw to clamp said elongate member in said slot;

and two nuts engaged with said bolt on opposite sides of said plate to adjust and secure the position thereof along said bolt.

6. Orthopaedic fracture fixation apparatus for use in association with two sets of bone pins respectively located on opposite sides of a fracture, said apparatus comprising: a circular cylindrical rod; two like universal joint assemblies respectively connected with opposite end portions of said rod, each such assembly including a connector part in the form of a ball with a radial projection therefrom and two plates apertured to partially receive said ball, one of said plates having said radial projection passed through the plate aperture, said plates being connected by screws to clamp said ball therebetween, said radial projection being bored to slidably receive the respective end portion of said rod, said radial projection having a screw to clamp said rod therein, one of said plates being of two-part construction with such parts having similar straight edge portions with a sequence of recesses therein and with such parts being screw connectable to clamp bone pins individually in corresponding pairs of said recesses; and an adjustment assembly including a bolt having a head in the form of a ring freely engaged over said radial projection screw clamp, a further plate bored to slidably receive said bolt and slotted to engage said rod with said rod and bolt disposed substantially parallel, a screw engaged with said further plate to clamp said rod in said slot, and two nuts threadably engaged on said bolt on respectively opposite sides of said further plate.

* * * * *